United States Patent [19]

Taninaka et al.

[11] 4,118,506
[45] Oct. 3, 1978

[54] PHARMACEUTICAL COMPOSITIONS CONTAINING 1,3-DITHIOL-2-YLIDENE MALONATE DERIVATIVES

[75] Inventors: Kuniaki Taninaka, Ibaragi; Hitoshi Kurono, Amagasaki; Tsutomu Kasai, Sakai, all of Japan

[73] Assignee: Nihon Nohyaku Co., Ltd., Tokyo, Japan

[21] Appl. No.: 799,027

[22] Filed: May 20, 1977

Related U.S. Application Data

[63] Continuation-in-part of Ser. No. 584,412, Jun. 6, 1975, abandoned.

[30] Foreign Application Priority Data

May 24, 1976 [ZA] South Africa ................. 76/3077

[51] Int. Cl.² ............................................. A61K 31/385
[52] U.S. Cl. ...................................................... 424/277
[58] Field of Search ........................................ 424/277

[56] References Cited

U.S. PATENT DOCUMENTS

| | | | |
|---|---|---|---|
| 3,761,596 | 9/1973 | Taninaka et al. | 424/277 |
| 3,856,814 | 12/1974 | Taninaka et al. | 424/277 |
| 3,876,663 | 4/1975 | Taninaka et al. | 424/277 |
| 4,035,387 | 7/1977 | Taninaka et al. | 424/277 |

Primary Examiner—Frederick E. Waddell
Attorney, Agent, or Firm—Karl W. Flocks

[57] ABSTRACT

A 1,3-dithiol-2-ylidene malonate derivative having the formula,

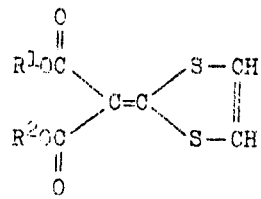

wherein $R^1$ and $R^2$, which may be same or different, represent individually a $C_1$–$C_4$ alkyl group has effects of stimulating, improving and recovering the functions of livers, and can prevent, alleviate and cure various liver damages of humans and animals when administered thereto either orally or parenterally.

31 Claims, No Drawings

PHARMACEUTICAL COMPOSITIONS CONTAINING 1,3-DITHIOL-2-YLIDENE MALONATE DERIVATIVES

The present application is a continuation-in-part of our copending application Ser. No. 584,412 filed June 6, 1975, first allowed and then withdrawn in favor of the present case and now abandoned.

This invention relates to a pharmaceutical composition for controlling liver damage of humans and animals.

More particularly, the invention is concerned with a pharmaceutical composition containing an effective amount of a compound having the general formula (I),

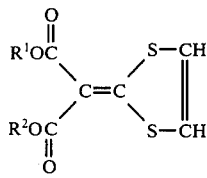
(I)

wherein $R^1$ and $R^2$, which may be same or different, represent individually a $C_1$–$C_4$ alkyl group.

The invention further relates to a pharmaceutical composition in the form of administration unit which contains a compound of the above-mentioned general formula (I) as active ingredient, either alone or in admixture with a pharmaceutically acceptable diluent.

The invention further pertains to a process for controlling the liver damages of humans and animals which comprises administering to the humans or animals a pharmaceutical composition in the form of administration unit which contains a compound of the above-mentioned general formula (I) as active ingredient, either alone or in admixture with a pharmaceutically acceptable diluent.

The term "controlling liver damage" or the like, referred to in the body and the claims, means to prevent, alleviate or cure various types of liver damage.

In view of its various functions, the liver is frequently called a delicate chemical factory. Thus, in the liver, various chemical reactions are being biochemically effected, such as detoxication, sugar metabolism, protein metabolism, lipid metabolism, formation and secretion of bile, control of hormones, formation of blood coagulant prothrombin, regeneration of liver cells, and storage of various living body-constituting elements (fats, glycogens, proteins and vitamins).

However, even such delicate and well-balanced functions of the liver sometimes undergo damage, either acutely or chronically, due to various factors such as alcohols, insufficient nutrition, viruses, chemicals, toxicants, etc. to cause such diseases as, for example, hepatitis, liver necrosis, fatty liver, cholestasis and hepatocirrhosis.

As the result of extensive studies, the present inventors have found that compounds represented by the aforesaid general formula (I) have actions to activate liver cells and to activate various metabolic functions of the liver, such as sugar metabolism, detoxication, formation and excretion of bile flow and biliary salts (choleratic action), and hence can improve the functions of damaged livers to provide such pharmacological effects as to alleviate or cure such damage and to protect the liver functions from certain damages.

An object of the present invention is to provide a novel pharmaceutical composition usable for controlling liver damage in humans and animals.

Another object of the invention is to provide a process for controlling liver damage in humans and animals.

Other objects and advantages of the invention will become apparent from the following description.

The compounds represented by the aforesaid general formula (I) are novel compounds, and can be synthesized, in practice, according to any of the two typical synthesis processes shown below by way of the reaction schemata (A) and (B).

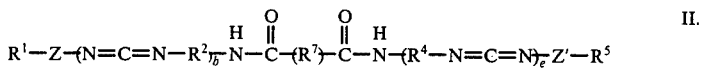
II.

wherein $R^1$ and $R^2$ are as defined previously; and X represents a halogen atom.

That is, according to this process, the compounds of the general formula (I) can be synthesized by reacting a malonic acid ester with carbon disulfide in the presence of a suitable base to form a dithiolate salt, reacting the dithiolate salt with a 1-acetoxy-1,2-dihalogenoethane to prepare a dialkyl 4-acetoxy-1,3-dithiolan-2-ylidene malonate, hydrolyzing the thus prepared malonate under proper conditions, and then subjecting the resulting dialkyl 4-hydroxy-1,3-dithiolan-2-ylidene malonate to dehydration reaction under proper conditions. The dehydration reaction is advantageously carried out in the presence of a dehydrating agent. Examples of the dehydrating agent include concentrated sulfuric acid, chlorosulfonic acid, methanesulfonic acid chloride, benzenesulfonic acid or its chloride, p-toluenesulfonic acid, phosphorus oxychloride, phosphorus pentachloride and phosphorus pentoxide, though these are not limitative. Further, examples of the inert solvent used in the dehydration reaction include carbon tetrachloride, benzene, and ethers, though these are not limitative.

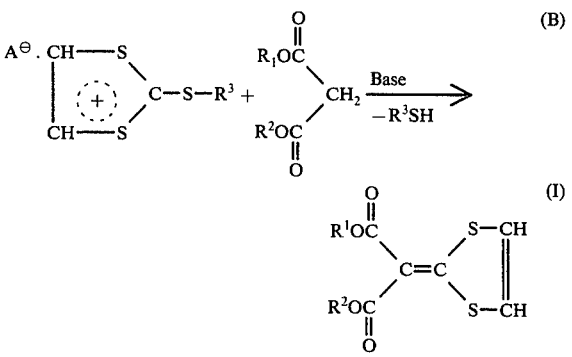

wherein $R^1$ and $R^2$ are as defined previously; $A^\ominus$ represents an anion residue; and $R^3$ represents an alkylating agent residue.

That is, according to this process, the compounds of the general formula (I) can be synthesized by reacting a dithiolium salt, which can be obtained by the reaction of 1,3-dithiol-2-thion with an alkylating agent or by the decarboxylation and simultaneous alkylation of a 1,3-dithiol-2-thion-4,5-dicarboxylic acid, with a malonic acid ester in the presence of a suitable base. Examples of the solvent used in the above reaction are alcohols, acetic acid, dimethyl formamide, dimethyl sulfoxide and tetrahydrofuran, though these are not limitative. Preferable as the base are alcoholates, sodium hydroxide, potassium hydroxide and sodium hydride, though these are not limitative.

Typical examples of the compounds represented by the general formula (I) are as shown in Table 1.

Table 1

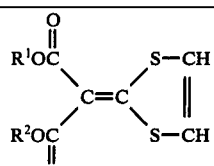

| Compound No. | $R^1$ | $R^2$ | m.p. or Refractive index |
|---|---|---|---|
| 1 | $CH_3$ | $CH_3$ | m.p. 134.5° – 135° C |
| 2 | $C_2H_5$ | $C_2H_5$ | m.p. 113° C |
| 3 | n-$C_3H_7$ | n-$C_3H_7$ | m.p. 73° – 75° C |
| 4 | i-$C_3H_7$ | i-$C_3H_7$ | m.p. 59° – 60° C |
| 5 | n-$C_4H_9$ | n-$C_4H_9$ | m.p. 55° – 57° C |
| 6 | i-$C_4H_9$ | i-$C_4H_9$ | m.p. 76° – 78° C |
| 7 | $C_2H_5$ | i-$C_3H_7$ | m.p. 57° – 58° C |
| 8 | $CH_3$ | i-$C_4H_9$ | $n_D^{20}$ 1.5928 |

The compounds represented by the general formula (I) are extremely low in toxicity to mammals, and their acute oral toxicity to male mice expressed as $LD_{50}$ values are at such a low toxicity level as in the range from 1,000 to 6,000 mg/kg or more, in general. For example, the $LD_{50}$ value of the compound 4 is 3,120 mg/kg. Further, these compounds have no detrimental effects on test animals administered therewith, so far as the doses thereof are within an ordinary administration range.

The compounds of the general formula (I) are usable as pharmaceuticals for humans and animals. They have broad and various pharmaceutical spectra. The compound of the formula (I) has effects of stimulating, improving and recovering the functions of livers, and can prevent, alleviate and cure various liver damages of humans and animals when administered thereto either orally or parenterally.

Experimental liver damages such as liver necrosis, hepatitis, fatty liver and hepatocirrhosis induced by administering chemicals such as carbon tetrachloride, chloroform, bromobenzene, dimethylnitrosamine, thioacetamide, allyl alcohol, D-galactosamine or ethionine to animals, have been acknowledged as the models of human liver damages against which pharmaceuticals are sought. The compounds of the present invention are effective against such liver damage.

Further, liver damage caused by toxic inorganic salts such as cadmium and selenium salts can be alleviated when the present compounds are administered.

Such compounds can show such main effects as described below.

(1) The compounds of the present invention have effects of not only preventing all of the above experimental damages but also alleviating or curing the experimental hepatitis, fatty liver and hepatocirrhosis. Thus, they will be appreciated as pharmaceuticals usable for those purposes.

(2) They have actions to stimulate the alcohol metabolic function of the liver to lower the concentration of alcohol in the blood, and hence are effective for promotion of recovery from alcoholic intoxication and for prevention, alleviation and therapy of crapulence.

(3) They have actions to stimulate the sugar metabolic function of the liver to lower abnormally elevated concentrations of sugar in the blood, and hence are effective as blood sugar depressants and curatives for diabetes.

(4) They have action to stimulate the formation and the excretion of bile flow or biliary salts.

(5) When cadmium or selenium salts are administered to animals, which have previously been administered with the said compounds, the toxic symptoms caused by said salts are far more alleviated than in the case of blank animals.

Accordingly, the compounds represented by the general formula (I) are effective as preventives, alleviatives and curatives for various liver damages including acute hepatitis, chronic hepatitis, fatty liver diseases, hepatocirrhosis, and chemical poisoning. For example, liver injury caused by administration of PAS (p-aminosalicyclic acid) can also be alleviated. Further, the said compounds are effective as depressants of alcohol in the blood, as blood sugar depressants, as diabetes curatives, as choleretics for inducing the formation and the excretion of bile flow or biliary salts, and as drugs for stimulating, promoting, improving and recovering metabolic functions of the livers.

Some of the effects mentioned above are confirmed by clinical tests.

In using the said compounds as the above-mentioned drugs, they may be formulated, according to usual procedures and means adopted in this field, into pharmaceutical compositions in the form of administration units convenient for their individual application purposes. That is, the said compounds are formulated into pharmaceutical compositions, either alone or in admixture with a pharmaceutically acceptable diluent, which may be any one of solids, semi-solids, liquids and intakable capsules, and are administered to humans or animals, either orally or parenterally or even by implantation or insertion into body cavities.

Thus, the present invention provides a pharmaceutical composition which comprises the above-mentioned compound as active ingredient and, in admixture therewith, a pharmaceutically acceptable solid, semi-solid or liquid diluent.

The present invention further provides a pharmaceutical composition containing as active ingredient the above-mentioned compound in the form of a sterile and/or isotonic aqueous solution.

The present invention still further provides a pharmaceutical composition in the form of administration unit which contains the above-mentioned compound either alone or in admixture with a pharmaceutically acceptable diluent.

The pharmaceutical compositions of the present invention can be provided in such various administration unit forms as powders, granules, tablets, sugar-coated tablets, pills, capsules, suppositories, suspensions, liquids, emulsions, ampoules and injections.

The present invention includes such mode that the above-mentioned compound as active ingredient may be administered singly.

The present invention further includes such mode that the above-mentioned compound may be administered in the form of a mixture with a pharmaceutically acceptable diluent. The diluent referred to herein means not only a mere diluent but also a pharmaceutically acceptable usual adjuvant. Examples of the mere diluent are those which are ordinarily used in the pharmaceutical field, and include such solid diluents as starch, lactose, calcium hydrogenphosphate, heavy magnesium oxide and the like, and such liquid diluents as water, isotonic solution, glucose solution and the like. Examples of the adjuvant include vehicles, extenders, binders, wetting agents, disintegrators, surfactants, lubricants, dispersants, buffer agents, seasonings, deodorants, dyes, flavors, preservatives and dissolution aids, though these are not limitative. These adjuvants may be used either singly or in the form of a mixture of two or more members.

The pharmaceutical composition of the present invention may be prepared according to any known method. For example, a mixture of the active ingredient and a diluent is formed, for example, into granules, and the thus formed granular composition is molded, for example, into tablets. In case the pharmaceutical composition is for parenteral administration, it is preferable to be made aseptic and, if necessary, be made isotonic to the blood.

Generally, the pharmaceutical composition of the present invention contains about 0.01 to 100% by weight, based on the weight of the composition, of the active compound. Thus, the present invention includes such mode that the said compound is used independently.

The pharmaceutical composition of the present invention may be incorporated with other pharmaceutically active compound. In some cases, the composition may be incorporated with a plurality of the present compounds.

For the control of various liver damages and various diseases derived therefrom, the pharmecutical composition of the present invention may be applied to humans and animals according to an ordinary procedure adopted in this field, in order to attain such effects as shown in the aforesaid animal tests. Thus, the composition of the present invention is administered orally or parenterally. The oral administration includes sublingual administration, and the parenteral administration includes administration by way of injection including, for example, subcutaneous, intramuscular and intravenous injections and installation.

The dose of the pharmaceutical of this invention varies depending on many factors, including the kind of subject (whether the pharmaceutical is administered to humans or to animals), the difference in susceptibility, age, sex, body weight, the clinical picture, the physical conditions of patients, the means of administration, the time and interval of administration, the kind and properties of pharmaceutical composition, the kind of active ingredient, etc. In some cases, accordingly, the dose of the pharmaceutical may be made smaller than the minimum dose mentioned below, while in other cases the dose would be in excess of the maximum dose mentioned below. In case the pharmaceutical is to be administered in a large dose, it is preferable that the pharmaceutical is divisionally administered several times a day.

In the case of oral administration, effective dose for animals is in the range from 0.1 to 500 mg, preferably from 1 to 100 mg, of active ingredient per one kilogram body weight per day. In the case of parenteral administration, effective dose for animals is in the range from 0.01 to 250 mg, preferably from 0.1 to 25 mg, of active ingredient per one kilogram body weight per day.

In the case of oral administration, effective dose for humans, deduced from the above-mentioned effective dose for animals with consideration for susceptibility difference and security, is advantageously in the range from 0.1 to 250 mg, preferably from 0.5 to 50 mg, per one kilogram body weight per day. In the case of parenteral administration, effective dose for humans is in the range from 0.01 to 100 mg, preferably from 0.1 to 25 mg, per one kilogram body weight per day.

The present invention is illustrated in more detail below with reference to examples including synthesis examples, but the invention is not limited to the examples.

Synthesis Example 1

Synthesis of diisopropyl 1,3-dithiol-2-ylidene malonate (Compound 4 in Table 1)

To a solution of 3 g of diisopropyl 4-hydroxy-1,3-dithiolan-2-ylidene malonate in 50 ml of carbon tetrachloride was added 1.2 g of chlorosulfonic acid, and the resulting mixture was continuously stirred at room temperature for 2 hours. After completion of the reaction, water was added to the reaction liquid, and the carbon tetrachloride layer was separated. The aqueous layer was extracted with ether, and then combined with the carbon tetrachloride layer. Subsequently, the combined layer was dried, and then the solvent was removed by distillation to form crystals. The thus formed crystals were collected and then dried to obtain 2.5 g of the above-mentioned compound in the form of white crystals, m.p. 59°–60° C., yield 86%.

Synthesis Example 2

Synthesis of disopropyl 1,3-dithiol-2-ylidene malonate (Compound 4 in Table 1)

A solution of 44.4 g (0.2 mole) of 1,3-dithiol-2-thion-4,5-dicarboxylic acid in 240 ml of nitromethane was heated to 80° C.. Into this solution, 100 ml of methyl iodide was gradually dropped, and the resulting mixture was refluxed for 6 hours. After completion of the reaction, the formed crystals were recovered by filtration, washed with 100 ml of ether and then air-dried to obtain 48 g of 2-methylthio-1,3-dithiolium iodide, m.p. 114°–116° C., (decomp.).

Separately, into a suspension of 1.1 g (0.03 mole) of 69% purity sodium hydride in 30 ml of dry tetrahydrofuran was gradually dropped with ice-cooling 5.6 g (0.03 mole) of diisopropyl malonate. After the generation of hydrogen gas from the resulting mixture had terminated, 8.2 g (0.03 mole) of the previously obtained 2-methylthio-1,3-dithiolium iodide was added to the mixture. Subsequently, the mixture was refluxed for 1 hour, and then the reaction liquid was poured into a large amount of ice water to deposit crystals. The crystals were recovered by filtration, dried, and then recrystallized from n-hexane to obtain 6.7 g of the above-mentioned compound in the form of white crystals, m.p. 59°–60° C., yield 77.5%.

In Examples 1 to 9 described below, all parts are by weight.

EXAMPLE 1

| | |
|---|---|
| Diethyl 1,3-dithiol-2-ylidene malonate (Compound 2) | 10 parts |
| Heavy magnesium oxide | 10 " |

-continued

| | |
|---|---|
| Lactose | 80 " |

The above-mentioned components were homogeneously mixed and pulverized to obtain a powder.

EXAMPLE 2

| | | |
|---|---|---|
| Di-n-propyl 1,3-dithiol-2-ylidene malonate (Compound 3) | 10 | parts |
| Synthetic aluminum silicate | 10 | " |
| Calcium hydrogenphosphate | 5 | " |
| Lactose | 75 | " |

The above-mentioned components were treated in the same manner as in Example 1 to obtain a powder.

EXAMPLE 3

| | | |
|---|---|---|
| Diisopropyl 1,3-dithiol-2-ylidene malonate (Compound 4) | 50 | parts |
| Starch | 10 | " |
| Lactose | 15 | " |
| Crystalline cellulose | 20 | " |
| Polyvinyl alcohol | 5 | " |
| Water | 30 | " |

The above-mentioned components were homogeneously kneaded, granulated, dried and sieved to obtain a granule.

EXAMPLE 4

99 Parts of the granule obtained in Example 3 was incorporated with 1 part of calcium stearate, and then subjected to compression molding to obtain a tablet of 10 mm in diameter.

EXAMPLE 5

| | | |
|---|---|---|
| Ethyl isopropyl 1,3-dithiol-2-ylidene malonate (Compound 7) | 95 | parts |
| Polyvinyl alcohol | 5 | " |
| Water | 30 | " |

The above-mentioned components were treated in the same manner as in Example 3 to obtain a granule. 90 Parts of the thus obtained granule was incorporated with 10 parts of crystalline cellulose, and then subjected to compression molding to obtain a tablet of 8 mm in diameter. Further, this tablet was formed into a sugar-coated tablet by use of proper amounts of a suspension comprising ethanolic shellac, syrup gelatin and precipitated calcium carbonate, and a dye.

EXAMPLE 6

| | | |
|---|---|---|
| Diisopropyl 1,3-dithiol-2-ylidene malonate (Compound 4) | 63 | parts |
| Calcium hydrogenphosphate | 20 | " |
| Crystalline cellulose | 10 | " |
| Calcium salt of carboxymethyl cellulose | 3 | " |
| Corn starch | 3 | " |
| Talc (Japanese Pharmacopoeia) | 1 | part |

The above-mentioned components were homogeneously mixed and the resulting mixture was introduced to a tablet machine to obtain tablets each containing 100 mg of the active ingredient.

EXAMPLE 7

| | | |
|---|---|---|
| Methyl isobutyl 1,3-dithiol-2-ylidene malonate (Compound 8) | 4 | parts |
| Nonionic surfactant | 10 | " |
| Isotonic sodium chloride solution | 86 | " |

The above-mentioned components were mixed together with heating to form a solution, which was then cooled to obtain an injection.

II.

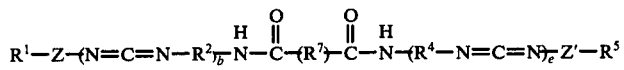

EXAMPLE 8

| | | |
|---|---|---|
| Diisopropyl 1,3-dithiol-2-ylidene malonate (Compound 4) | 0.5 | part |
| Nonionic surfactant | 2.5 | parts |
| Distilled water for injection | 97.0 | " |

The above-mentioned components were treated in the same manner as in Example 6 to obtain an injection.

EXAMPLE 9

The powder obtained in Example 1 was filled into commercially available capsules to obtain a capsule.

EXAMPLE 10

Protective Effect on Acute Liver Damage associated with Centrilobular Necrosis (Experimental Model using Carbon Tetrachloride)

Carbon tetrachloride ($CCl_4$) administration induces centrilobular necrosis of the liver associated with loss of diphosphopyridine nucleotide, hepatic glycogen, coenzyme A and increase in neutral fat. Release of several enzymes from the hepatocytes, and increase of enzyme activities in the plasma are recognized as the result of the damage of the liver. A suitable means for evaluating the degree of damage induced by $CCl_4$ or the degree of protection afforded by drugs is to study the plasma glutamic-pyruvic transaminase (p-GPT) activity.

Methods: The test compounds were dissolved or suspended in olive oil and administered orally at the dose of 250 mg/kg to the mice (Four-week-old male mice-dd strain). After 6 hours, $CCl_4$ was administered orally (0.05 ml/kg as olive oil solution). Animals were killed 24 hours after $CCl_4$ administration, and the liver was grossly observed. The plasma was obtained by centrifugation. Activities of p-GPT were determined by the method of Reitman and Frankel and expressed in Karmen units.

Score for liver damage index was as follows:

| Liver damage index | Description |
|---|---|
| 0 | Normal |
| 2 | Slightly recognized |
| 4 | Clearly observable damage |
| 6 | Heavy damage |

Each figure indicates average of 5 to 6 mice. Values of p-GPT over 1,000 Karmen unit regarded as 1,000 for calculation of average for convenience.

Results:

Table 2

Protective effect on acute liver damage associated with centrilobular necrosis

| Compound No. | Liver Damage Index | p-GPT |
|---|---|---|
| 1 | 0.4 | 138 |
| 2 | 0.2 | 36 |
| 3 | 0.1 | 36 |
| 4 | 0.0 | 36 |
| 5 | 0.4 | 52 |
| 6 | 0.4 | 75 |
| 7 | 0.8 | 102 |
| 8 | 0.6 | 88 |
| Carbon tetrachloride alone | 5.2 | >1,000 |
| Thioctic acid amide | 4.8 | 763 |
| Anethol trithion | 1.6 | 38 |
| Control | 0.0 | 36 |

Carbon tetrachloride is best suitable for bringing test animals to the state of acute hepatitis. As is clar from the results of tests carried out by use of carbon tetrachloride, all the active ingredients used in the present composition shown prominent liver damage-preventing effects, and are comparable in effectiveness to thioctic acid amide and anethol trithion which are commercially available at present as liver drugs.

Accordingly, the compounds of this invention are useful as pharmaceutical for human and animal acute hepatitis.

EXAMPLE 11

Protective Effect on Actue Liver Damage associated with Centrilobular Necrosis (Experimental Models using Bromobenzene, Dimethylnitrosamine and Chloroform)

Bromobenzene (hereinafter abbreviated as BB), Dimethylnitrosamine (hereinafter abbreviated as DMN) and chloroform (hereinafter abbreviated as CF) resemble carbon tetrachloride in inducing liver damage associated with centrilobular necrosis.

TESTING METHOD

Test compound or anethol trithion was orally administered to animal at the dose of 100 mg/kg. Six hours after it, the hepatotoxin was administered at such a dose and via such a route as shown in Table 3. Twenty four hours after it (in the case of dimethylnitrosamine, exceptionally fifteen hours after it) the animals were sacrificed and blood samples were collected. Indices of hepatotoxicity adoptable in each chemical were measured, from which the efficacy of the compound was evaluated.

Table 3

Administration of hepatotoxin and index of hepatotoxicity

| Hepatotoxin | Animal | Dose (ml/kg) | Route | Index of hepatotoxicity |
|---|---|---|---|---|
| BB | male rat (SD) | 0.75 | oral | p-GPT activity BSP test |
| DMN | male mouse (4 week-old, dd) | 0.05 | intraperitoneal | p-GPT activity BSP test |
| CF | male mouse (4 week-old, dd) | 0.2 | oral | p-GPT activity |

RESULTS

Similarly to carbon tetrachloride, BB, DMN and CF are known to be hepatotoxins inducing centrilobular necrosis. As shown in Table 4, Compound 4 of this invention normalized the indices of hepatotoxicity to demonstrate its high efficacy for preventing liver damage.

In addition, it was superior to anethol trithion in this effect.

Thus, it is evident that the compound of this invention is useful as a pharmaceutical for controlling human and animal liver diseases accompanied with centrilobular necrosis.

Table 4

Protective effects on acute liver damages associated with centrilobular necrosis

| Hepatotoxin | Index of hepatotoxicity | Control | Positive control* | Compound 4** | Anethol trithion** |
|---|---|---|---|---|---|
| BB | p-GPT (Karmen unit) | 16 ± 1.9 | 53 ± 27 | 23 ± 3.7 | 28 ± 4.1 |
|  | BSP (mg/dl) | 2.7 ± 1.7 | 20.4 ± 7.1 | 10.6 ± 4.5 | 12.9 ± 5.5 |
| DMN | p-GPT | 15 ± 1.5 | >600 | 204 ± 44 | 192 ± 54 |
|  | BSP | 1.5 ± 0.3 | 31.2 ± 5.9 | 10 ± 2.0 | 17.6 ± 2.7 |
| CF | p-GPT | 20 ± 3.0 | 432 ± 58 | 58 ± 15 | >1000 |

*Hepatotoxin alone was administered.
**After treatment with Compound 4 or anethol trithion, the hepatotoxin was administered.

EXAMPLE 12

Therapeutic Effect on Chronic Liver Damage (Experimental Model using Thioacetamide)

Thioacetamide (hereinafter abbreviated to "TAA") also causes liver damages in animals, like carbon tetrachloride, and hence is frequently used as a chemical for bringing about hepatitis and fatty liver diseases. In the tests of this Example, TAA was repeatedly administered to animals to prepare test animals suffering from somewhat chronic liver damages, and then the present compounds were administered thereto to know whether or not the compounds were effective against chronic hepatitis.

The degree of the liver damage and the therapeutic effects of the compounds were evaluated according to BSP test. The BSP test is a method in which BSP (sulfobromophthalein sodium), a dye known to be quickly metabolized in and excreted from the liver, is intravenously injected into animals and, after a definite period of time, the blood is taken out to measure the amount of BSP remaining in the plasma. In case the animals are suffering from the liver damage, the dye will remain, according to the degree of the damage, at the stage where a major portion of BSP is metabolized and excreted in the case of normal animals.

Five groups of rats (Sprague Dawley strain) were treated as follows:

Group A: The rats were orally administered with 100 mg/kg of thioacetamide, at 3 days intervals for 36 days (12 times of the administration), then were submitted for 10 days to a normal diet.

Group B: The rats were orally administered with 100 mg/kg of thioacetamide at 3 days intervals for 36 days (12 times of the administration), then were submitted for 10 days to the normal diet + 0.2% of compound 4.

Group C: The rats were submitted to the normal diet as the control.

Five rats were sacrificed from each group at appropriate intervals for BSP (sulfobromophthalein sodium) test, the results of which were shown as amounts (mg) of BSP remaining in 1dl of plasma.

Table 5

| Time of Sacrifice | Therapeutic effect on chronic liver damage | | |
|---|---|---|---|
| | Group A | Group B | Group C |
| 24 hr. after 4 times TAA administration | 18.2 ± 2.6 | | 0.3 ± 0.1 |
| 24 hr. after 8 times TAA administration | 16.8 ± 5.2 | | — |
| 24 hr. after 12 times TAA administration | 17.3 ± 4.4 | | 0.8 ± 0.1 |
| After compounds administration | | | |
| 2 Days | 12.7 ± 3.7 | 7.2 ± 2.5 | 0.4 ± 0.1 |
| 5 Days | 8.7 ± 1.9 | 2.8 ± 0.7 | — |
| 10 Days | 1.4 ± 0.4 | 0.5 ± 0.1 | 0.6 ± 0.1 |

By the repeated administration of TAA, the concentration of BSP in the blood increased to 16 to 19 mg/dl and the said level lasted, and therefore it is considered that the rats were brought to a state close to chronic hepatitis. After the administration of TAA, the present compound-administered group (Group B) was quicker in cure of liver damage than the unadministered group (Group A). This indicates that the present compound is effective against chronic hepatitis as well.

EXAMPLE 13

Protective Effect on Acute Liver Damage associated with Periportal Necrosis (Experimental Model using Allyl Alcohol)

Testing method

The compound of this invention or anethol trithion was orally administered to the male mouse (4 week/old, dd strain) at the dose of 250 mg/kg. Six hours after it, allyl alcohol was orally administered at the dose of 0.075 ml/kg. Twenty four hours after it, the animals were sacrificed to collect blood samples. BSP test revealed the residual quantity of BSP, from which the protective effect of the compound of this invention was evaluated.

Results

Table 6

| Hepatotoxin | Index of hepatotoxicity | Protective effect on acute hepatitis | | | |
|---|---|---|---|---|---|
| | | Control | Positive control* | Compound 4** | Anethol trithion** |
| Allyl alcohol | BSP | 1.8 ± 0.4 | 28.4 ± 4.8 | 17 ± 3.2 | 19.3 ± 4.6 |

*Hepatotoxin alone was administered.
**After treatment with Compound 4 or anethol trithion, the hepatotoxin was administered.

Allyl alcohol differs from carbon tetrachloride or bromobenzene, dimethylnitrosamine or chloroform in that it induces liver damage associated with periportal necrosis. As shown in Table 6, the compound of this invention protected the liver against this damage.

Accordingly, the compound of this invention is useful as a pharmaceutical for human or animal liver disease accompanied with periportal necrosis.

EXAMPLE 14

Protective Effect on Acute Hepatitis associated with Mesenchymal Reaction and Discrete Lobular Necrosis (Experimental Mode using D-Galactosamine)

D-Galactosamine is a compound which induces a discrete lobular necrosis associated with mesenchymal reaction similar to the change observed in human viral hepatitis, so that it is frequently used in producing a model for viral hepatitis.

Methods

The compound of this invention or anethol trithion was administered orally to the male rat (SD strain) at the dose of 250 mg/kg. Six hours after it, D-galactosamine was intraperitoneally administered at the dose of 600 mg/kg. Four hours after it, an additional 300 mg/kg was administered intraperitoneally. Eight hours after it, the animals were sacrificed to collect the blood samples. P-GPT activity and triglyceride in the liver were measured to evaluate the effect of the compound of this invention.

Results

Table 7

| Hepatotoxin | Index of hepatotoxicity | Protective effect on acute liver damage associated with discrete lobular necrosis | | | |
|---|---|---|---|---|---|
| | | Control | Positive control* | Compound 4** | Anethol trithion** |
| D-Galactosamine | p-GPT (Karmen unit) | 13 ± 0.5 | 92 ± 59 | 51 ± 15 | 106 ± 30 |
| | Triglyceride in the liver (mg/g) | 6.5 ± 1.2 | 8.2 ± 2.2 | 4.4 ± 0.68 | 9.2 ± 1.5 |

*Hepatotoxin alone was administered.
**After treatment with Compound 4 or anethol trithion, the hepatotoxin was administered.

As shown in Table 7, the compound of this invention protected the liver from damage by D-Galactosamine.

Accordingly, the compound of this invention is useful as a pharmaceutical for use in therapy for human or animal hepatitis accompanied with mesenchymal reaction and discrete lobular necrosis.

EXAMPLE 15

Effect on Fatty Liver (Experimental Model using Ethionine)

There are known many factors inducing fatty liver. But, the fatty liver is grouped into a couple of patterns from the mechanism of lipid accumulation or metabolism of lipoprotein in the liver. Ethionine is a typical example which induces first pattern of fatty liver. It inhibits RNA and protein synthesis and destroys polysome of the liver cell. Fatty liver is induced by inhibition of the protein synthesis and disturbance of lipoprotein secretion.

Usually, fatty liver is closely related to the accumulation of triglyceride in the liver. In the present example, the degree of fatty liver and protective or therapeutic effect on the fatty liver was evaluated by measurement of triglyceride content in the liver.

METHODS

The compounds of this invention and methionine were independently dissolved or suspended into olive oil and administered orally to the male mouse (4 week-old dd-strain) at the dose of 250 mg/kg. One hour before it, simultaneously with it or one hour after it, ethionine dissolved in equimolar NaOH solution was administered intraperitoneally at the dose of 200 mg/kg. Twenty four hours after the administration of ethionine, the animals were sacrificed and triglyceride content in the liver was determined by chromotropic acid method.

Results

Table 8

| Group | Effect on fatty liver | |
|---|---|---|
| | Number of animals | Triglyceride (mg/g-liver) |
| Control | 14 | 4.0 ± 0.33 |
| Ethionine | 14 | 13.6 ± 1.08 |
| Compound 4 → 1 hr. → Ethionine | 14 | 9.1 ± 1.15 |
| Compound 4 → 0 hr. → Ethionine | 15 | 5.4 ± 0.61 |
| Ethionine → 1 hr. → Compound 4 | 15 | 10.0 ± 1.15 |
| Methionine → 0 hr. → Ethionine | 15 | 10.3 ± 0.83 |

As above, the compounds of this invention depress the abnormal accumulation of triglyceride, induced by ethionine, in the liver to exhibit a protective and therapeutic effect on fatty liver. The compounds of this invention are superior to methionine in the above-mentioned effect. Accordingly, the compounds of this invention are useful as pharmaceutical for human and animal fatty liver.

EXAMPLE 16

Therapeutic Effect on Fatty Liver (Experimental Model using Carbon Tetrachloride)

Carbon tetrachloride also induces fatty liver, but the picture of disease differs from the case of ethionine-induced fatty liver. Carbon tetrachloride is generally considered to damage microsome and thereby to inhibit protein synthesis and induce fatty liver.

Methods

Carbon tetrachloride was subcutaneously administered to 36 week-old male rats (SD strain) for 4 days at the dose of 1 ml/kg. The treated animals were left for 3 days after the last administration to maximize the manifestation of fatty liver.

Administration of Compound 4 was commenced on the fourth day after the administration of carbon tetrachloride was completed. It was orally given everyday for 10 days at the dose of 50 or 250 mg/kg. On the 11th day, the animals were sacrificed by exsanguination. The therapeutic effect was evaluated by determining the content of lipid in the liver (triglyceride and total lipid) and examining the histopathological changes. Triglyceride and total lipid were determined colorimetrically by chromotropic acid method and Bragdon's oxidation method, respectively.

Indices for the histopathological change is as follows:

| Index | Histopathological changes |
|---|---|
| − | Normal |
| ± | Formation of small droplet deposition of lipid but the number of droplet is not so many. |
| + | Formation of small or slightly fused droplet deposition of lipid and increasing the number of droplet |
| ++ | Formation of fused large droplet deposition of lipid |

Results

Table 9

| | Therapeutic effect on fatty liver | |
|---|---|---|
| Group | Triglyceride (mg/g-liver) | Total lipid (mg/g-liver) |
| Control | 13.0 ± 3.6 | 64.3 ± 8.3 |
| Positive control | 50.9 ± 8.9 | 151.3 ± 24.0 |
| Compound 4 (50 mg/kg) | 37.6 ± 8.5 | 78.6 ± 16.8 |
| Compound 4 (250 mg/kg) | 23.6 ± 7.0 | 64.1 ± 10.2 |
| Methionine (250 mg/kg) | 47.3 ± 7.3 | 146.1 ± 13.0 |

Table 10

| Therapeutic effect on fatty liver (Histopathological examination) | | | | | | | |
|---|---|---|---|---|---|---|---|
| Group | Degree of fatty liver | | | | | | |
| Control | − | − | − | − | − | | |
| Positive control | + | + | + | + | ++ | | |
| Compound 4 (50 mg/kg) | + | ± | ± | ± | ± | − | ± |
| Compound 4 (250 mg/kg) | − | − | ± | ± | ± | ± | − |
| Methionine (250 mg/kg) | + | ± | ++ | + | ++ | + | + |

As shown in Table 9, the group "Positive control" to which carbon tetrachloride was administered but thereafter the compound of this invention was not administered manifested a high degree of fatty liver and showed no sign of improvement.

On the other hand, in the therapeutic groups to which the compound of this invention was given at the dose of 50 or 250 mg/kg the degree of fatty liver was significantly improved. In other words, the compound of this invention exhibited a therapeutic effect.

On the contrary, methionine hardly exhibited a therapeutic effect against fatty liver induced by carbon tetrachloride.

Table 10 illustrates the results of histopathological examination. The size and number of lipid droplet decreased in the groups therapied with the compounds of this invention, demonstrating an alleviation of fatty liver.

Accordingly, the compound of this invention is useful as pharmaceutical for fatty liver in humans and animals.

EXAMPLE 17

Therapeutic Effect on Cirrhosis

Almost all the liver diseases induced by various causes are considered to advance, finally, to cirrhosis. Cirrhosis is a final stage of liver damage, which is difficult to classify from the causal viewpoint. Usually, experimental cirrhosis is induced by long-term repeated administration of carbon tetrachloride. The therapeutic effect of the compounds of this invention on cirrhosis, which had been caused by carbon tetrachloride administration, was examined.

Methods

A 10% solution of carbon tetrachloride in olive oil was administered to the male rat (4 week-old SD-strain) intraperitoneally at the dose of 0.5 ml carbon tetrachloride/kg twice a week over a period of 10 weeks, to induce cirrhosis. Four days after the final administration of carbon tetrachloride, the formation of pseudo-lobulus was confirmed. Then the diseased animals were divided into two groups. Therapeutic group was submitted a diet containing 2000 ppm of Compound 4, while the positive control group was submitted a normal diet. Control group, to which olive oil alone had been administered, was submitted a normal diet.

At 1, 2, 4 and 8 weeks after beginning of Compound 4 feeding, 5 animals from each group were sacrificed, and the therapeutic effect on cirrhosis was evaluated by examining plasma transaminase activity (p-GPT and p-GOT, Reitman-Frankel method) and observing histopathological changes.

Degree of cirrhosis in the histopathological examination was graded as follows:

| Index | Histopathological changes |
| --- | --- |
| − | Normal |
| ± | Slight formation of pseudo-lobulus |
| + | Slight formation of pseudo-lobulus, and slight fibrosis |
| ++ | Moderate formation and cohesion of pseudo-lobulus, moderate fibrosis |
| +++ | Severe cohesion of pseudo-lobulus, severe fibrosis |

It was considered that all the animals had reached the stage of cirrhosis after carbon tetrachloride was administered for a period of ten weeks. As shown in Table 11, the compound rapidly normalized plasma transaminase activity, both p-GPT and p-GOT.

Table 12 illustrates the therapeutic effect on cirrhosis. In the positive control group a moderate to high degree of cirrhosis including fibrosis of liver, appearance of pseudo-lobulus and its cohesion was observed over a period of 8 weeks after the final administration of carbon tetrachloride. On the contrary, in the therapeutic group the cohesion of pseudo-lobulus and the fibrosis were ameliorated after two weeks had passed, demonstrating the therapeutic effect of the compound on cirrhosis. Thus, the compound in this invention is useful as pharmaceutical for therapy in chronic liver diseases and cirrhosis in humans and animals.

EXAMPLE 18

Cholagogic Action

Formation and excretion of biliary salts in the bile outflow are the important metabolic functions of the liver. If the bile flow is damaged by some cause, cholestasis and several types of liver diseases accompanying jaundice will be induced.

Drugs as choleretics are used for patients to improve bile flow. In the present example, the effect of the compound of the invention on the quantities of bile and biliary salt is investigated.

Methods

The male rat (4 week-old, SD-JCL strain) was anesthetized with sodium pentobarbital (37.5 mg/kg, intraperitoneal injection). The abdominal cavity was opened through a midline incision. The common bile duct was catheterized with polyethylene tube o.d. 0.8 mm. The catheter was brought to the outside through the abdominal incision wound prior to closing. Bile was collected from the catheter continuously with time intervals of one hour. The quantity of bile produced in one hour was determined by weighing and that of biliary salt was determined by enzymatic method (Ikagaku Jikkenho Koza 1B, Biological Constituents II, edited by Tamino YAMAKAWA). The amount of biliary salts was represented as chloic acid equivalent.

Table II

| | Therapeutic effect on cirrhosis (Transaminase activity) | | | | | |
| --- | --- | --- | --- | --- | --- | --- |
| Period of therapy (week) | p-GPT activity (Karmen unit) | | | p-GOT activity (Karmen unit) | | |
| | Control | Positive control | Therapeutic group | Control | Positive control | Therapeutic group |
| 0 | 28 ± 3 | 262 ± 46 | | 79 ± 6 | 658 ± 127 | |
| 1 | 33 ± 2 | 184 ± 26 | 169 ± 30 | 93 ± 8 | 728 ± 136 | 562 ± 119 |
| 2 | 29 ± 3 | 76 ± 14 | 43 ± 11 | 90 ± 5 | 263 ± 28 | 182 ± 43 |
| 4 | 32 ± 4 | 47 ± 21 | 45 ± 23 | 83 ± 7 | 206 ± 46 | 142 ± 48 |
| 8 | 30 ± 2 | 40 ± 20 | 33 ± 20 | 85 ± 6 | 190 ± 30 | 120 ± 32 |

Table 12

| | Therapeutic effect on cirrhosis (Histopathological examination) | | | | | | | | | | | | | | |
| --- | --- | --- | --- | --- | --- | --- | --- | --- | --- | --- | --- | --- | --- | --- | --- |
| Period of therapy (week) | Control | | | | | Positive control | | | | | Therapeutic group | | | | |
| 0 | − | − | − | − | − | ++ | +++ | ++ | + | ++ | | | | | |
| 1 | | | | | | ++ | +++ | +++ | ++ | ++ | + | +++ | ++ | ++ | ++ |
| 2 | | | | | | + | ++ | +++ | + | ++ | + | + | ± | ± | ++ |
| 4 | | | | | | +++ | ++ | ++ | + | +++ | ± | ± | + | + | ± |
| 8 | | | | | | ++ | ++ | ++ | ++ | +++ | ± | ± | ± | ± | ± |

In the representation of the results, the quantities of bile and biliary salts produced in one hour prior to the administration of drug were taken as 100. The compound of this invention was orally administered at the dose of 200 mg/kg. As reference, anethol trithion was used.

Results

Table 13

Effect on bile flow

| | Experiment 1 | | Experiment 2 | |
|---|---|---|---|---|
| Time | Control | Compound 4 (200 mg/kg) | Control | Anethol trithion (200 mg/kg) |
| Before treatment 1 hour | 100 | 100 | 100 | 100 |
| After treatment | | | | |
| 1 hour | 100 ± 2.4 | 115 ± 4.5 | 104 ± 3.5 | 114 ± 15 |
| 2 | 104 ± 6.5 | 122 ± 7.6 | 101 ± 4.9 | 114 ± 15 |
| 3 | 92 ± 6.4 | 117 ± 7.1 | 93 ± 6.9 | 102 ± 11 |
| 4 | 88 ± 9.7 | 114 ± 8.2 | 84 ± 6.7 | 95 ± 7.7 |
| 5 | 85 ± 9.3 | 102 ± 9.2 | 76 ± 6.6 | 86 ± 6.6 |

Table 14

Effect on the excretion of biliary salt

| | Experiment 1 | | Experiment 2 | |
|---|---|---|---|---|
| Time | Control | Compound 4 (200 mg/kg) | Control | Anethol trithion (200 mg/kg) |
| Before treatment 1 hour | 100 | 100 | 100 | 100 |
| After treatment | | | | |
| 1 hour | 89 ± 6.6 | 108 ± 15 | 94 ± 6.2 | 108 ± 12 |
| 2 | 92 ± 11 | 132 ± 25 | 89 ± 9.5 | 89 ± 11 |
| 3 | 66 ± 8.8 | 138 ± 27 | 77 ± 11 | 66 ± 3.8 |
| 4 | 54 ± 15 | 117 ± 27 | 56 ± 9.7 | 47 ± 3.0 |
| 5 | 46 ± 16 | 90 ± 21 | 52 ± 10 | 33 ± 4.0 |

As shown in Table 13, bile flow was elevated by the administration of the compound of this invention. Quantity of total excreted bile for 5 hours after administration of Compound 4 was 1.2 times greater than that in control. In the case of anethol trithion the quantity of total excreted bile was 1.1 times greater than that in control.

As shown in Table 14, the amount of excreted biliary salts was remarkably increased by the administration of the compound of this invention. Amount of total biliary salts excreted for 5 hours after administration of Compound 4 was 1.7 times greater than that in control. In the case of anethol trithion, however, no particular increase was observed in the excretion of biliary salt. In other words, the compound of this invention is particularly effective in promoting the excretion of biliary salt.

The compound of this invention is to be classified as drug for increasing the excretion of biliary salts, namely cholanertica, and their effectiveness to the diseases of human or animal liver or bile duct can readily be expected from the hitherto reported findings concerning the behavior of anethol trithion. As above, the compound of this invention can stimulate the metabolic function of the liver and therefore is useful as pharmaceutical for controlling liver diseases caused by cholestasis.

EXAMPLE 19

Effect on Concentration of Ethyl alcohol in the Blood

The test compounds are dissolved or suspended in olive oil and administered orally at the dose of 250 mg/kg to the mice. After 6 hours, 1,000 mg/kg of ethyl alcohol was given orally. Blood was taken in a capillary from caudal vein at the time indicated in the results. The plasma was obtained by centrifugation. The concentration of ethyl alcohol in the plasma was measured by FID type gas liquid chromatography. Five mice were used for each group.

Results

Table 15

Concentration of Ethyl alcohol in Plasma (ppm)

| Time (min.) | Control | Compound Pre-treated | |
|---|---|---|---|
| | | Compound 4 | Compound 7 |
| 0 | 27 ± 17 | 25 ± 12 | 30 ± 14 |
| 5 | 875 ± 203 | 582 ± 143 | 830 ± 180 |
| 15 | 810 ± 191 | 468 ± 30 | 799 ± 154 |
| 30 | 690 ± 214 | 220 ± 87 | 448 ± 208 |
| 60 | 167 ± 76 | 29 ± 17 | 158 ± 113 |
| 120 | 5 ± 1 | not detected | 12 ± 2 |

The concentration of ethyl alcohol in the plasma of the present compound-treated mice was lower than that of normal mice. This tendency was particularly marked at the stages of 30, 60 and 120 minutes after administration of ethyl alcohol, and thus it is understood that the amount of ethyl alcohol in the treated mice decreased quickly. Further, the present compound-treated mice were obviously quicker in recovery of intoxicated state, when observed visually. This indicates that by administration of the present compounds, the mice were stimulated in alcohol metabolic function of liver.

EXAMPLE 20

Effect on glucose metabolism:

Methods: The test compounds dissolved in olive oil and administered orally at the dose of 250 mg/kg to the mice. After 6 hours, 4.0 g/kg of glucose was orally administered. The same amount of glucose was given to the control animals. 0.02 ml of blood was taken from caudal vein of the mice at 30, 60, 90 and 120 min. after glucose administration. Blood sugar was measured by the procedure of Somogyi-Nelson. Number of animals used was 5 to 6 mice for each treatment.

Results

Table 16

| | Blood Sugar (mg/dl) | | |
|---|---|---|---|
| Time (min.) | Control | Test compound Pre-treatment | |
| | | Compound 2 | Compound 4 |
| 0 | 145 ± 11.8(100%) | 136 ± 20.4(100%) | 123 ± 10.9(100%) |
| 30 | 311 ± 21.9(214%) | 295 ± 22.3(217%) | 282 ± 25.2(229%) |
| 60 | 290 ± 14.6(200%) | 251 ± 19.6(185%) | 236 ± 19.7(192%) |
| 90 | 263 ± 13.1(181%) | 202 ± 12.3(149%) | 159 ± 18.3(129%) |
| 120 | 251 ± 13.5(173%) | 158 ± 15.5(116%) | 138 ± 14.4(112%) |

The blood sugar values of the each group showed peaks after 30 minutes, and no substantial difference was seen in the peak values. Thereafter, however, obvious difference was observed in the recovery of blood sugar value, and the present compound-treated groups were quicker in recovery. This indicates that by administration of the present compounds, the mice were stimulated in glucose metabolic function of liver.

EXAMPLE 21

Clinical Test on Liver Injury and Chronic Hepatitis

Test Method

Six patients were used for the test. One was diagnosed as liver injury caused by administration of PAS (p-aminosalicyclic acid) for three months and five were diagnosed as chronic hepatitis by doctor.

The tablets obtained in Example 6 were orally administered to the respective patients at the dose of twelve tablets a day (four tablets after every meal).

Curing effects on the liver injury and chronic hepatitis after administration were evaluated by measuring plasma transaminase activity (p-GPT and p-GOT).

The results obtained are as shown in Table 17.

Table 17

| Patient No. | Disease | Sex | Age | Administration period | p-GPT activity (Karmen Unit) | p-GOT activity (Karmen Unit) |
|---|---|---|---|---|---|---|
| 1 | Liver injury | Male | 61 | Before administration | 270 | 270 |
|  |  |  |  | After 3 days | 215 | 270 |
|  |  |  |  | After 4 days | 169 | 231 |
|  |  |  |  | After 7 days | 94 | 81 |
|  |  |  |  | After 12 days | 41 | 36 |
|  |  |  |  | After 15 days | 24 | 37 |
|  |  |  |  | After 19 days | 21 | 24 |
| 2 | Chronic hepatitis | " | 30 | Before administration | 270 | 270 |
|  |  |  |  | After 14 days | 62 | 68 |
|  |  |  |  | After 35 days | 43 | 24 |
| 3 | " | " | 42 | Before administration | 163 | 145 |
|  |  |  |  | After 14 days | 96 | 100 |
|  |  |  |  | After 56 days | 87 | 77 |
| 4 | Chronic hepatitis | Male | 37 | Before administration | 185 | 80 |
|  |  |  |  | After 2 days | 113 | 60 |
|  |  |  |  | After 9 days | 94 | 68 |
|  |  |  |  | After 16 days | 62 | 49 |
|  |  |  |  | After 62 days | 33 | 33 |
| 5 | " | Female | 42 | Before administration | 94 | 95 |
|  |  |  |  | After 8 days | 119 | 78 |
|  |  |  |  | After 28 days | 79 | 65 |
|  |  |  |  | After 30 days | 57 | 57 |
| 6 | " | Male | 48 | Before administration | 354 | 83 |
|  |  |  |  | After 14 days | 306 | 108 |
|  |  |  |  | After 23 days | 121 | 48 |
|  |  |  |  | After 36 days | 65 | 33 |
|  |  |  |  | After 56 days | 53 | 24 |
|  |  |  |  | After 82 days | 39 | 24 |

As is clear from Table 17, the compound 4 of this invention is useful for normalizing plasma transaminase activity (p-GPT and p-GOT). (The values of p-GPT and p-GOT for a healthy human are less than 40 Karmen Unit, respectively.)

The foregoing description of specific embodiments will so fully reveal the general nature of the invention that others can, by applying current knowledge, readily modify and/or adapt such specific embodiments for various applications, without departing from the generic concept and, therefore, such adaptations and modifications should and are intended to be comprehended within the meaning and range of equivalents of the disclosed embodiments. It is to be understood that the phraseology or terminology employed herein is for the purpose of description and not of limitation.

What is claimed is:

1. A pharmaceutical composition for preventing liver necrosis, for preventing and curing hepatitis or fatty liver, for curing hepatocirrhosis, and for formation and excretion of bile flow or biliary salt, containing an effective amount sufficient for said purpose of a compound having the general formula,

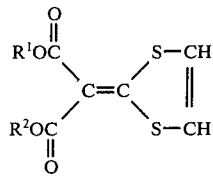

wherein $R^1$ and $R^2$, which may be same or different, represent individually a $C_1$-$C_4$ alkyl group, and a pharmaceutically acceptable diluent.

2. The pharmaceutical composition according to claim 1 which comprises the said compound and a pharmaceutically acceptable diluent.

3. The pharmaceutical composition according to claim 1 which contains the said compound in an amount of 0.01 to 100% by weight.

4. The pharmaceutical composition according to claim 1, wherein the said compound is diethyl 1,3-dithiol-2-ylidene malonate.

5. The pharmaceutical composition according to claim 1, wherein the said compound is ethyl isopropyl 1,3-dithiol-2-ylidene malonate.

6. The pharmaceutical composition according to claim 1, wherein the said compound is diisopropyl 1,3-dithiol-2-ylidene malonate.

7. The pharmaceutical composition according to claim 2, wherein the compound is formulated into an administration unit form.

8. The pharmaceutical composition according to claim 7, wherein the administration unit form is any one of powder, granule, tablet, pill, sugar-coated tablet, capsule, ampoule, suppository, suspension, liquid, emulsion or injection.

9. The pharmaceutical composition according to claim 7, wherein the said compound is diethyl 1,3-dithiol-2-ylidene malonate.

10. The pharmaceutical composition according to claim 7, wherein the said compound is ethyl isopropyl 1,3-dithiol-2-ylidene malonate.

11. The pharmaceutical composition according to claim 7, wherein the said compound is diisopropyl 1,3-dithiol-2-ylidene malonate.

12. A process for preventing liver necrosis, for preventing and curing hepatitis or fatty liver, for curing hepatocirrhosis, and for formation and excretion of bile flow or biliary salt of animals including humans, which comprises orally or parenterally administering to the animal an effective amount sufficient for said purpose of a compound having the general formula,

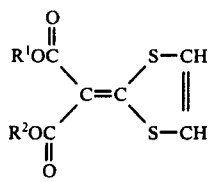

wherein $R^1$ and $R^2$, which may be same or different, represent individually a $C_1$-$C_4$ alkyl group.

13. The process of claim 12, wherein the administration is carried out parenterally.

14. The process of claim 13, wherein the dose for animals is in the range from 0.01 to 250 mg per kg body weight per day.

15. The process of claim 13, wherein the dose for humans is in the range from 0.01 to 100 mg per kg body weight per day.

16. The process of claim 12, wherein the administration is carried out orally.

17. The process of claim 16, wherein the dose for animals is in the range from 0.1 to 500 mg per kg body weight per day.

18. The process of claim 16, wherein the dose for humans is in the range from 0.1 to 250 mg per kg body weight per day.

19. The process of claim 12, wherein the compound is diethyl 1,3-dithiol-2-ylidene malonate.

20. The process of claim 12, wherein the compound is ethyl isopropyl 1,3-dithiol-2-ylidene malonate.

21. The process of claim 12, wherein the compound is diisopropyl 1,3-dithiol-2-ylidene malonate.

22. A process for lowering the concentration of alcohol in the blood of animals including humans comprising administering orally or parenterally to the animal an effective amount sufficient for said purpose of a compound having the general formula,

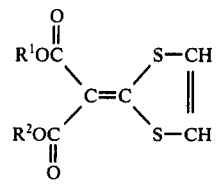

wherein $R^1$ and $R^2$, which may be same or different, represent individually a $C_1$-$C_4$ alkyl group.

23. The process of claim 22, wherein the compound is diethyl 1,3-dithiol-2-ylidene malonate.

24. The process of claim 22, wherein the compound is ethyl isopropyl 1,3-dithiol-2-ylidene malonate.

25. The process of claim 22, wherein the compound is diisopropyl 1,3-dithiol-2-ylidene malonate.

26. A process for treating diabetes in animals including humans comprising administering orally or parenterally an effective blood-sugar depressant amount to said animal for stimulating the sugar metabolic function of liver to lower the abnormally elevated concentration of sugar in the blood, of a compound having the general formula,

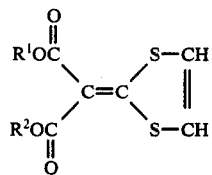

wherein $R^1$ and $R^2$, which may be same or different, represent individually a $C_1$-$C_4$ alkyl group.

27. The process of claim 26, wherein the compound is diethyl 1,3-dithiol-2-ylidene malonate.

28. The process of claim 26, wherein the compound is ethyl isopropyl 1,3-dithiol-2-ylidene malonate.

29. The process of claim 26, wherein the compound is diisopropyl 1,3-dithiol-2-ylidene malonate.

30. The process of claim 12, wherein said necrosis, fatty liver, hepatocirrhosis, or hepatitis is induced by chemical poisoning.

31. The process of claim 30, wherein the chemical causing said poisoning is carbon tetrachloride, chloroform, bromobenzene, dimethylnitrosamine, thioacetamide, ethionine, a cadmium salt or a selenium salt.

* * * * *

UNITED STATES PATENT OFFICE
CERTIFICATE OF CORRECTION

Patent No. 4,118,506                    Dated October 3, 1978

Inventor(s) Kuniaki TANINAKA, Hitoshi KURONO and Tsutomu KASAI

It is certified that error appears in the above-identified patent and that said Letters Patent are hereby corrected as shown below:

Column 2, after line 18, the formula should read as follows:

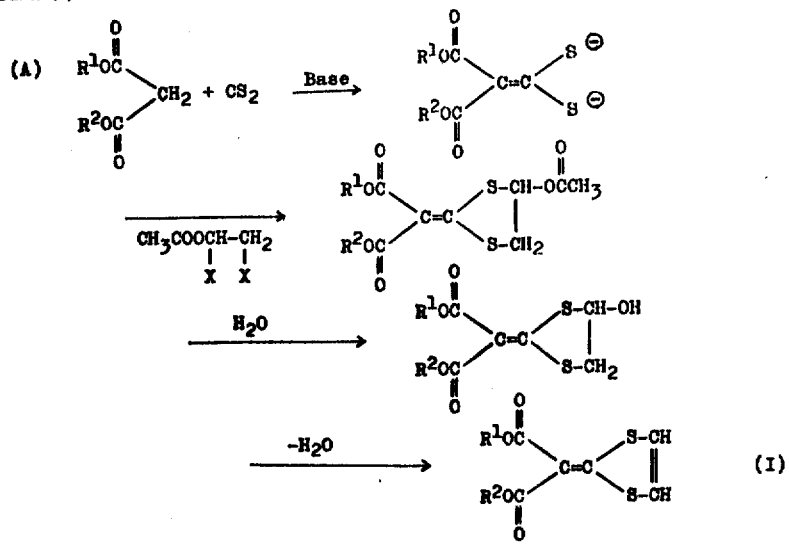

Column 7, after Example 2, lines 15 to 18, delete the formula.

Signed and Sealed this

*Twenty-fifth* Day of *March 1980*

[SEAL]

*Attest:*

SIDNEY A. DIAMOND

*Attesting Officer*        *Commissioner of Patents and Trademarks*